United States Patent [19]

Jon et al.

[11] Patent Number: 5,646,813
[45] Date of Patent: Jul. 8, 1997

[54] METHOD AND APPARATUS FOR REDUCING ESD DURING THERMAL SHOCK TESTING

[75] Inventors: Min-Chung Jon, Princeton Junction; Douglas Charles Smith, Rumson, both of N.J.; Joseph Charles Veshinfsky, Catasauqua, Pa.

[73] Assignee: Lucent Technologies Inc., Murray Hill, N.J.

[21] Appl. No.: 398,244

[22] Filed: Mar. 3, 1995

[51] Int. Cl.⁶ .............................. H05F 3/02; G01N 25/18
[52] U.S. Cl. ..................... 361/220; 73/865.6; 374/57
[58] Field of Search ................................ 361/212, 220, 361/215; 174/35 R, 35 MS; 324/453, 454; 73/865.6; 165/48.1, 61; 374/45, 57; 206/709

[56] References Cited

U.S. PATENT DOCUMENTS

| | | | |
|---|---|---|---|
| 4,519,718 | 5/1985 | Staffin et al. | 374/45 |
| 4,694,375 | 9/1987 | Devins et al. | 361/212 |
| 4,779,163 | 10/1988 | Bickford et al. | 361/212 |
| 4,928,201 | 5/1990 | Wright | 361/215 |
| 5,290,101 | 3/1994 | Englert et al. | 374/57 |

*Primary Examiner*—Fritz Fleming
*Attorney, Agent, or Firm*—Robert B. Levy

[57] ABSTRACT

Electrostatic discharge during thermal shock testing on an electronic device (12) by alternate immersion in hot and cold baths (14, 16) of a fully-fluorinated liquid (20) can be reduced by carrying the device within a first, electrically conductive, open-weave basket (32) enclosed within, and coupled to a second basket (30) of similar construction, but a looser weave. The first basket acts as a Faraday shield about the electronic device when both baskets are alternately immersed in the hot and cold baths.

12 Claims, 1 Drawing Sheet

Fig. 1 (Prior Art)
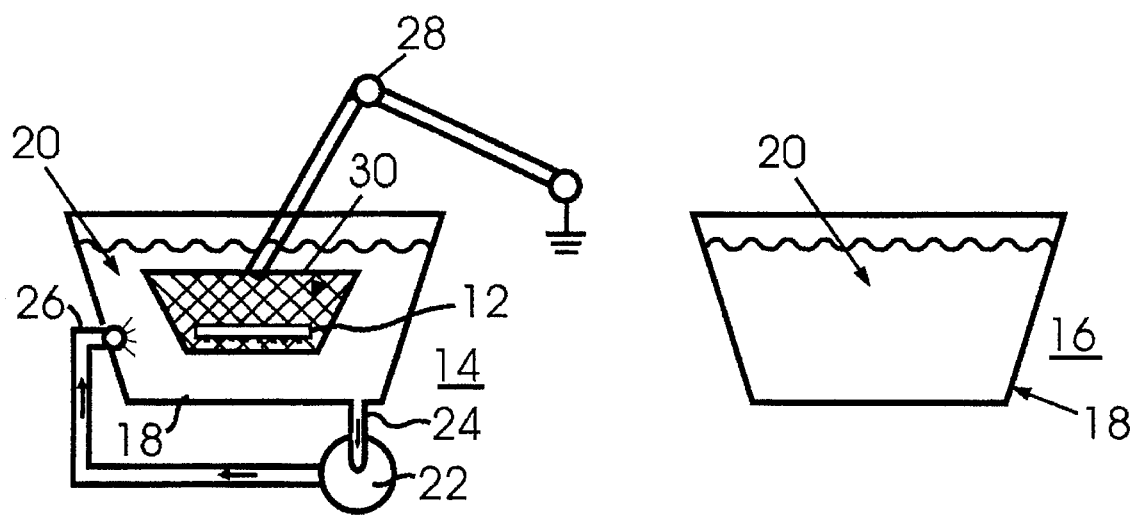
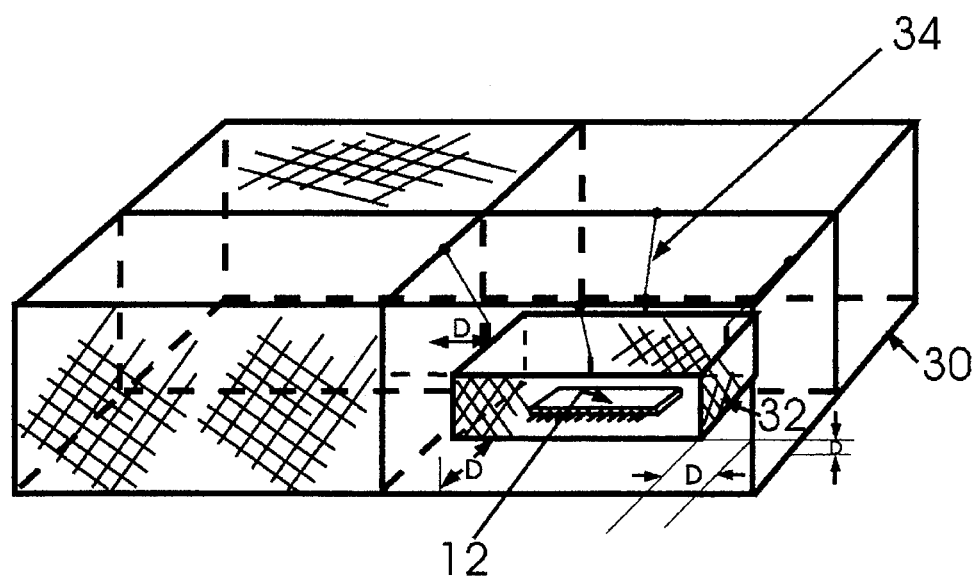
Fig. 2

METHOD AND APPARATUS FOR REDUCING ESD DURING THERMAL SHOCK TESTING

TECHNICAL FIELD

This invention relates to a technique for reducing, if not eliminating, the incidence of Electrostatic Discharge (ESD) during thermal shock testing of electronic devices by alternate immersion in hot and cold baths.

BACKGROUND ART

Both integrated circuits, as well as circuit boards (hereinafter referred to collectively as "electronic devices"), are commonly subjected to thermal shock testing during design qualification. Such thermal shock testing is typically accomplished by placing an electronic device in a metallic basket (e.g., stainless steel) that is alternately immersed in hot and cold liquid baths that circulate constantly to assure a uniform temperature in each bath. The hot bath is usually more than 130° C. whereas the cold bath is at least −60° C. To provide a robust test for thermal shock, the basket is transported between the hot and cold baths for 15 to 100 cycles, with a dwell time in each bath of approximately five minutes.

In practice, the hot and cold baths are filled with a fully-fluorinated liquid hydrocarbon, such as FLUORINERT liquid available from 3M Company, St. Paul, Minn. When the cold bath is filled with such a fluorinated hydrocarbon liquid, a static electric potential as much as 10,000 volts may be generated within an inch or so from the surface of the cold bath upon the immersion of the device. Such a potential will damage the electronic device in the basket, which is undesirable.

Past attempts at eliminating the excess charge have included reducing the turbulence within the cold bath by blocking one or more inlets through which the liquid is circulated. However, reducing the flow of liquid can damage the pump that circulates the liquid within the bath. Rather than block some of the inlets, a smaller size pump could be used. However, the disadvantage with using a smaller size pump is that such a pump may not sufficiently circulate the fluid to achieve a fairly uniform bath temperature. Other attempts at eliminating ESD have included ionizing the bath by way of a high-voltage supply. Although moderately effective, ionizing the bath generally entails extensive modification to the equipment employed to carry out thermal shock testing.

Thus, there is a need for a technique for mitigating ESD during thermal shock testing by alternately immersing a device in hot and cold liquid baths.

BRIEF SUMMARY OF THE INVENTION

Briefly, in accordance with the invention, a technique is disclosed for testing an electronic device for thermal shock while reducing, if not eliminating, the incidence of electrostatic discharge occurring during such testing. The method of the invention is initiated by placing the device in a first, electrically conductive, open-weave enclosure situated inside of, and electrically coupled to a second, electrically conductive open-weave enclosure whose weave is looser than the first enclosure. Both the first and second enclosures are alternately immersed in hot and cold liquid baths such that upon immersion in each bath, the second enclosure contacts the liquid in each bath prior to the first enclosure. In this way any electrostatic charge at the surface of each bath will be dissipated by the second enclosure before the charge reaches the first enclosure. Thus, the potential damage to the device within the first enclosure is reduced, if not eliminated, because the first enclosure advantageously serves as a Faraday Cage that shields the device carded within it from ESD.

BRIEF SUMMARY OF THE DRAWINGS

FIG. 1 is a block schematic diagram of a machine, in accordance with the prior art, for thermally shock testing an electronic device; and FIG. 2 is a front view, in perspective, of a basket, as modified in accordance with the invention, for use with the apparatus of FIG. 1.

DETAILED DESCRIPTION

FIG. 1 illustrates a prior art machine 10 for thermally shock testing at least one electronic device 12, such as circuit board or integrated circuit. The machine 10 typically comprises a cold liquid bath 14 and a hot bath 16. Each of the baths 14 and 16 comprises a tank 18 filled with a fully fluorinated hydrocarbon liquid 20, such as FLUORINERT liquid. The liquid 20 within the tank 18 of the cold bath 14 is circulated by a pump 22, usually of the constant displacement variety. The pump 22 draws the liquid 20 from the tank 18 through an inlet 24 coupled to the tank bottom. The liquid is then discharged back into the tank 18 through an outlet 26 near the tank top. A pump (not shown), similar to the pump 22, is provided for circulating the liquid 20 within the hot bath 16. The liquid 20 in the cold bath 14 is typically maintained at a temperature of about −60° C. by a refrigeration unit (not shown) while the liquid in the hot bath 16 is typically maintained at a temperature of about 130° C. by a heater (not shown).

In addition to the hot and cold baths 14 and 16, respectively, the machine 10 also includes an articulated arm 28 having an electrically conductive, open-weave basket 30 mounted to its end. The basket 30 is formed from a stainless steel mesh having a weave that is sized to permit one or more devices to be received in the basket without falling therethrough, yet permit the liquid 18 to enter the basket relatively quickly when the basket is immersed in each of the baths 14 and 16. The basket 30 is coupled to circuit ground through the arm 28.

The machine 10 functions in the following manner. Initially, the transporter arm 28 displaces the basket 30 to a load/unload position at which the basket lies outside of the cold and hot baths 14 and 16 respectively. While the basket 30 is in its load/unload position, an operator (not shown) loads the basket with at least one device 12. Thereafter, the arm 28 displaces the basket 28 alternately between the cold and hot baths 14 and 16, respectively, a plurality of times (typically between fifteen and one hundred cycles). Typically, the basket 30 dwells in each bath for a approximately five minutes. In this way, each device 12 within the basket 30 is heated and cooled repeatedly, thus subjecting it to thermal shock as is often required to evaluate the extent to which the device design is robust. Once the basket has been alternately immersed in the cold and hot baths 14 and 16, respectively, the desired number of cycles, then the arm 28 is displaced to its load/unload position to permit the operator to remove each device 12 from the basket 30.

The devices 12 that are thermally shock tested in the manner described often suffer from electrostatic discharge (ESD) upon immersion into the cold bath 14. At −60° C., the FLUORINERT liquid 20 in the tank 18 forming the cold bath 14 has a volume resistivity on the order of $10^{18}$ ohm/square, making it an excellent insulator. As a consequence, the liquid 20 of the cold bath 14 dissipates very little charge. Agitating the liquid 20 within the cold bath has been found to produce a large static charge near the top of the liquid. The amount of the charge can be significant. Thus, when a device 12 is immersed within the liquid 20 of the cold bath 14, the charge may pass to the device, causing it to be damaged.

Referring now to FIG. 2, the problem of ESD damage to each device 12 during thermal shock testing can be advantageously ameliorated by modifying the basket 30 to include a second basket 32 inside of it for receiving each device 12. Like the outer basket 30, the inner basket 32 is fabricated from a stainless steel mesh. However, as compared to the outer basket 30, the inner basket 32 has a much tighter weave. In other words, the openings in the mesh forming the basket 32 are far smaller as compared to openings in the mesh forming the basket 30. Typically, the openings in the mesh forming the basket 32 are no more than one-half the size of the openings in the basket 30.

The inner basket 32 is sized to fit within the basket 30 so that a gap D of at least one inch (2.54 cm) exists between them in all directions. Although the basket 32 is physically spaced from the outer basket 30 as described, the inner basket is supported within the outer basket by a set of ribs 34—34. Each rib 34 typically comprises a stainless steel wire or rod that is soldered at each of its ends to the inner and outer baskets 30 and 32, respectively. In this way, the inner basket 32 is grounded through the outer basket 30.

The inner basket 32 ameliorates potential ESD damage to each device 12 placed within it because the inner basket acts as a Faraday cage about the device. Since the inner basket 32 is physically separated from the outer basket 30 by the gap D, the outer basket contacts the liquid 20 of the cold bath 14 first. Any charge on or near the surface of the liquid 20 of the cold bath 14 will pass to, and dissipate in, the outer basket 30 before reaching the device 12 in the inner basket 32. Hence, the likelihood that such a charge will pass to the device is significantly reduced.

The foregoing describes a technique for reducing the incidence of ESD during thermal shock testing of a device 12 by placing the device in a first (inner) basket 32 surrounded by an second (outer) basket 30 before alternately immersing both baskets in the hot and cold baths 14 and 16.

It is to be understood that the above-described embodiments are merely illustrative of the principles of the invention. Various modifications and changes may be made thereto by those skilled in the art which will embody the principles of the invention and fall within the spirit and scope thereof.

What is claimed is:

1. A method of minimizing electrostatic discharge during thermal shock testing of an electronic device, the method characterized in the steps of:

disposing said electronic device within the interior of a first electrically conductive enclosure;

disposing said first electrically conductive enclosure within the interior of a second electrically conductive enclosure; and immersing said first and second electrically conductive enclosures in a liquid on which electrostatic charge may build up on the surface of said liquid, said first and second electrically conductive enclosures being such that the first electrically conductive enclosure acts as a Faraday cage for said device, whereby at least a substantial portion of any electrostatic charge that may be on the surface of said liquid will be precluded from passing to said device.

2. The invention of claim 1 wherein said liquid is a fully fluorinated hydrocarbon liquid.

3. The invention of claim 1 wherein said first electrically conductive enclosure is a first conductive basket and said second electrically conductive enclosure is a second conductive basket.

4. The invention of claim 3 wherein the first conductive basket is spaced away from any portion of said second conductive basket by at least approximately one inch.

5. The invention of claim 4 wherein said first conductive basket is held in fixed relation to said second basket by a plurality of electrically conductive ribs.

6. The invention of claim 3 wherein the mesh of the first conductive basket is substantially finer than the mesh of said second conductive basket.

7. A method comprising the steps of:

disposing a first electrically conductive mesh basket within the interior of a second electrically conductive mesh basket; and immersing an electronic device contained in said first electrically conductive mesh basket in a liquid on which electrostatic charge may build up on the surface of said liquid, when said first electrically conductive mesh basket is initially immersed in said liquid, a substantial portion of any electrostatic charge that may be on the surface of the liquid will pass to, and dissipate in, said second electrical conductive mesh basket and will not reach said device.

8. The invention of claim 7 wherein said liquid is a fully fluorinated hydrocarbon liquid.

9. The invention of claim 7 wherein the first conductive basket is spaced away from any portion of said second conductive basket by at least approximately one inch.

10. The invention of claim 9 wherein said first conductive basket is held in fixed relation to said second conductive basket by a plurality of electrically conductive ribs.

11. The invention of claim 9 wherein the mesh of the conductive basket is substantially finer than the mesh of said second conductive basket.

12. An apparatus for minimizing electrostatic discharge during thermal shock testing of an electronic device, the apparatus comprising:

a first electrically conductive enclosure for disposing in its interior said electronic device;

a second electrically conductive enclosure for disposing in its interior said first electrically conductive enclosure; and means for immersing said first and second electrically conductive enclosures in a liquid on which electrostatic charge may build up on the surface of said liquid, said first and second electrically conductive enclosures being arranged such that the first electrically conductive enclosure acts as a Faraday cage for said device, and whereby at least a substantial portion of any electrostatic charge that may be on the surface of said liquid will be precluded from passing to said device.

* * * * *